United States Patent [19]

Schacht et al.

[11] 4,051,173

[45] Sept. 27, 1977

[54] PHENOXYALKANOL DERIVATIVES

[75] Inventors: Erich Schacht; Werner Mehrhof; Zdenek Simane; Herbert Nowak, all of Darmstadt, Germany

[73] Assignee: Merck Patent Gesellschaft mit beschrankter Haftung, Darmstadt, Germany

[21] Appl. No.: 694,447

[22] Filed: June 9, 1976

Related U.S. Application Data

[63] Continuation of Ser. No. 564,474, April 2, 1975, abandoned.

[30] Foreign Application Priority Data

Apr. 2, 1974   Germany ............................ 2415867

[51] Int. Cl.² .................... C07C 69/06; C07C 43/20
[52] U.S. Cl. ............................ 560/255; 260/613 R; 260/287 R; 260/289 R; 260/345.5; 260/326.47; 260/326.1; 260/326.5 M; 260/293.83; 260/327 R; 424/341; 424/311; 424/274; 424/267; 424/258
[58] Field of Search ................. 260/613 R, 488 CD

[56] References Cited

U.S. PATENT DOCUMENTS 3,363,003   1/1968   Bolhofer ............................ 260/613
3,804,839   4/1974   Dahm et al. ....................... 260/539 X
3,981,905   9/1976   Adams et al. ................ 260/613 R X

FOREIGN PATENT DOCUMENTS 621,255   11/1963   Belgium ........................... 260/613 D Primary Examiner—Bernard Helfin
Attorney, Agent, or Firm—Millen & White

[57]   ABSTRACT

Phenoxylakanols of the formula

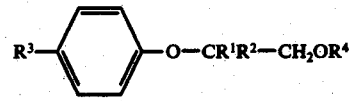

wherein $R^1$ is H or $CH_3$; $R^2$ is $CH_3$ or $C_6H_5$; $R^3$ is 4-Hal-phenoxymethyl, 1,2,3,4-tetrahydro-1-naphthyl, 1-pyrryl, piperidino, isoindoline, 1,2,3,4-tetrahydroquinoline, 1,2,3,4-tetrahydro-1-$R^5$-4-quinolyl, 4-chromanyl, 4-thiochromanyl, or, when at least one of $R^1$ and $R^2$ is other than $CH_3$, also Hal, phenyl, 4-Hal-phenyl or 4-Hal-phenoxy, wherein $R^4$ is H or alkanoyl of 2-4 carbon atoms, $R^5$ is H or $CH_3$ and Hal if F, Cl or Br; and physiologically acceptable acid addition salts thereof possess pharmacological activity, particularly cholesterol, triglyceride and uric acid blood-level lowering activity and are also useful as intermediates for the production of the corresponding phenoxyacetic acids.

11 Claims, No Drawings

PHENOXYALKANOL DERIVATIVES

This is a continuation of application Ser. No. 564,474, filed Apr. 2, 1975 and now abandoned.

BACKGROUND OF THE INVENTION

The invention relates to novel phenoxyalkanol derivatives.

The compounds of this invention are intermediates for the production of 2-p-substituted phenoxypropionic acids. See the applications of Schacht et al., Ser. No. 497,300 filed Aug. 14, 1974, and Ser. No. 449,332 filed Mar. 8, 1974, and U.S. Pat. No. 3,804,839.

Similar compounds are known from Dutch Pat. application No. 6,506,443.

SUMMARY OF THE INVENTION

In a composition aspect, this invention relates to novel phenoxyalkanol derivatives of the general Formula I

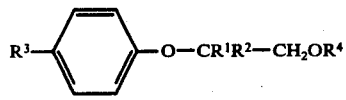

I wherein $R^1$ is H or $CH_3$; $R^2$ is $CH_3$ or $C_6H_5$; $R^3$ is 4-Hal-phenoxymethyl, 1,2,3,4-tetrahydro-1-naphthyl, 1-pyrryl, piperidino, isoindolino, 1,2,3,4-tetrahydroquinolino, 1,2,3,4-tetrahydro-1-$R^5$-4-quinolyl, 4-chromanyl, 4-thiochromanyl, or, when at least one of $R^1$ and $R^2$ is other than $CH_3$, also Hal, phenyl, 4-Hal-phenyl or 4-Hal-phenoxy, wherein $R^4$ is H or alkanoyl of 2-4 carbon atoms, $R^5$ is H or $CH_3$ and Hal is F, Cl or Br; and physiologically acceptable acid addition salts thereof.

In another composition aspect, this invention relates to pharmaceutical compositions comprising a novel phenoxyalkanol derivative of this invention in admixture with a pharmaceutically acceptable carrier.

In process aspects, this invention relates to processes for the production of the novel compounds of this invention and their use as pharmaceutically active agents.

DETAILED DISCUSSION

In addition to a halogen atom or a heterocyclic group named above, $R^3$ can be one of the carbocyclic groups, 4-Hal-phenoxymethyl, 1,2,3,4-tetrahydro-1-naphthyl and, when $R^1$ is H or $R^2$ is phenyl, also phenyl, 4-Hal-phenyl and 4Hal-phenoxy. Each such heterocyclic group, the halogen substituents and the carbocyclic substituents are contemplated subclasses of this invention.

In Formula I, $R^3$ preferably is 4-Hal-phenoxy-methyl, 1,2,3,4-tetrahydroquinolino, 1,2,3,4-tetrahydro-1-$R^5$-4-quinolyl, 4-chromanyl or 4-thiochromanyl and, additionally, when at least one of $R^1$ and $R^2$ is other than $CH_3$, also phenyl, 4-Hal-phenyl or 4-Hal-phenoxy. $R^4$ is preferably H or acetyl, especially H. Hal is preferably F or, more preferably, Cl.

Accordingly, in a preferred embodiment, the invention relates to compounds of Formulae I and Ia-Ii in which at least one of $R^1$-$R^5$ has one of the preferred values indicated above. Some of these preferred groups of compounds can be expressed by the following partial formulae Ia to Ii, which otherwise correspond to Formula I but wherein:

I(a) $R^3$ is 4-Hal-phenoxymethyl or, when $R^1$ and $R^2$ are not both $CH_3$, also phenyl, 4-Hal-phenyl or 4-Hal-phenoxy;

I(b) $R^3$ is 1,2,3,4-tetrahydroquinolino or 1,2,3,4-tetrahydro-1-$R^5$-4-quinolyl;

I(c) $R^3$ is 4-chromanyl or 4-thiochromanyl;

I(d) $R^3$ is 4-Hal-phenoxymethyl or $R^4$ is H or acetyl;

I(e) $R^4$ is H;

I(f) $R^3$ is 4-Hal-phenoxymethyl or, if $R^1$ and $R^2$ are not both $CH_3$, also phenyl, 4-Hal-phenyl or 4-Hal-phenoxy and $R^4$ is H;

I(g) $R^3$ is 1,2,3,4-tetrahydroquinolino or 1,2,3,4-tetrahydro-1-$R^5$-4-quinolyl and $R^4$ is H;

I(h) $R^3$ is 4-chromanyl or 4-thiochromanyl and $R^4$ is H; and

I(i) $R^3$ is 4-Hal-phenoxymethyl and $R^4$ is H.

In a process aspect, this invention relates to a process for the preparation of phenoxyalkanol derivatives of Formula I and of their physiologically acceptable acid addition salts, wherein a. a phenol of the general Formula II

II wherein $R^3$ has the values given above, is reacted with a compound of the general Formula III

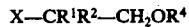

III wherein X is Cl, Br, I, OH or esterified OH and $R^1$, $R^2$ and $R^4$ have the values given above, or b. in a compound of general Formula IV

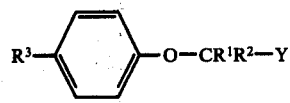

IV wherein Y is a radical which can be converted into the group —$CH_2OR^4$ and $R^1$, $R^2$ and $R^3$ have the values given above, the radical Y is converted into the group —$CH_2OR^4$.

Optionally, thereafter, in a resulting product of Formula I, an alkanolyoxy group is saponified and/or a hydroxyl group is esterified and/or a resulting compound of Formula I is converted into one of its physiologically acceptable acid addition salts by treatment with an acid.

In Formula III, X is preferably Cl or Br, but can also be, in addition to free OH and I, esterified OH, in particular reactive esterified OH, for example, alkylsulphonyloxy with, in particular, 1-6 carbon atoms (for example, methanesulphonyloxy), arylsulphonyloxy, in particular of 6-10 carbon atoms (for example, benzenesulphonyloxy, p-toluenesulphonyloxy, 1- or 2-naphthalenesulphonyloxy) or acyloxy, in particular alkanoyloxy, preferably of 1-7 carbon atoms (for example, acetoxy, heptanoyloxy or benzoyloxy). In Formula IV, Y is preferably COOH; alkoxycarbonyl, wherein alkoxy preferably is of 1-4 carbon atoms, in particular methoxycarbonyl or ethoxycarbonyl; CHO; $CH_2Hal$, such as $CH_2Cl$, $CH_2Br$ or $CH_2I$; an esterified or etherified $CH_2OH$ group, the ester or ether part of which generally is of up to 10, preferably up to 7 carbon atoms, for example, acyloxymethyl, in particular, alkanoyloxymethyl, for example, acetoxymethyl, propionyloxymethyl or benzoyloxymethyl, alkoxymethyl such as methoxymethyl, tetrahydropyranyl-2-oxymethyl or benzyloxymethyl; and aminoethyl.

As used hereinafter, Ac is alkanoyl of 2-4 carbon atoms.

In other respects, the preparation of the compounds of Formula I is carried out in accordance with methods which are known in the art, such as are described in the literature (for example, in standard works such as Houben-Weyl, Methoden der organischen Chemie (Methods of Organic Chemistry, Georg Thieme Verlag, Stuttgart), and in particular, under the reaction conditions which are known and suitable for the reactions mentioned.

If desired, the starting compounds for the preparation of the compounds of Formula I can also be formed in situ and not isolated from the reaction mixture but reacted immediately to give a compound of Formula I.

The compounds of Formulae II and III are for the most part known. The phenols II can be obtained, for example, by splitting their methyl ethers and the alcohols and esters III can be obtained from compounds of the general formula X—CR$^1$R$^2$—Y by converting the radical Y into the group —CH$_2$OR$^4$ in accordance with the methods indicated further below.

The phenol II can initially be converted into a salt, in particular into a metal salt, for example, an alkali metal salt, preferably Li, Na or K salt. To form the salt, the phenol can be reacted with a reagent which forms metal salts, for example, an alkali metal, e.g., Na, an alkali metal hydride or an alkali metal amide, e.g., LiH, NaH, NaNH$_2$ or KNH$_2$, an alkali metal alcoholate, e.g., lithium methylate, ethylate or tert.-butylate, sodium methylate, ethylate or tert.-butylate or potassium methylate, ethylate or tert.-butylate, an organo-metallic compound, e.g., butyl-lithium, phenyl-lithium or phenyl-sodium, a metal hydroxide, carbonate or bicarbonate, e.g., lithium hydroxide, carbonate or bicarbonate, sodium hydroxide, carbonate or bicarbonate, potassium hydroxide, carbonate or bicarbonate or calcium hydroxide, carbonate or bicarbonate. The salt or II is advantageously prepared in the presence of a solvent, for example, a hydrocarbon, e.g., hexane, benzene, toluene or xylene, an ether, e.g., diethyl ether, diisopropyl ether, tetrahydrofuran (THF), dioxan or diethylene glycol dimethyl ether, an amide, e.g., dimethylacetamide, dimethylformamide (DMF) or phosphoric acid hexamethyltriamide, an alcohol, e.g., methanol, ethanol, isopropanol, or tert.-butanol, a ketone, e.g., acetone or butanone or also a solvent mixture.

The phenol II or preferably a salt thereof, is reacted with a compound of Formula III, preferably in the presence of a diluent, for example, in the presence of the solvent which has been used for the preparation of the salt, but which can be replaced by another solvent or diluted therewith. The reaction is usually carried out at temperatures between −20° and 150° C., preferably between 20° and 120° C. and most preferably at the boiling point of the solvent. It can be carried out under an inert gas, for example, nitrogen. The phenolate can also be formed in situ and in this case the phenol II and the compound III are allowed to react with one another in the presence of the reagent which forms the salt. In a particularly preferred method, compounds II and III (X = Cl or Br) are boiled together with an alcoholic (for example, ethanolic) sodium alcoholate solution for several hours.

It is also possible to react a free phenol II with an alcohol of Formula III (R$^4$ = Ac, X = OH), preferably in the presence of a condensation agent. Examples of suitable condensation agents are acid dehydration catalysts, for example, mineral acids, e.g., sulphuric acid or phosphoric acid, and also arylsulphonyl chlorides, arsenic acid, boric acid, sodium sulphate or potassium sulphate, as well as diaryl carbonates (for example, diphenyl carbonate), dialkyl carbonates (for example, dimethyl carbonate or diethyl carbonate) or carbodiimides (for example, dicyclohexylcarbodiimide). When an acid is used as the condensation agent, the reaction is preferably carried out in an excess of this acid without the addition of a further solvent, at temperatures between about 0° and about 100° C., preferably between 50° and 60° C. However, diluents, for example, one of the abovementioned solvents, can also be added. When a carbonic acid ester is used, the reaction is preferably carried out at a higher temperature, preferably between about 100° and about 210° C., it being possible, if desired, to add a trans-esterification catalyst such as sodium carbonate or potassium carbonate or sodium methylate.

The compounds of Formula I can also be obtained by converting the radical Y in a compound of Formula IV into the group —CH$_2$OR$^4$.

More specifically, for this purpose, compounds of Formula IV, wherein Y is a free or functionally modified, in particular esterified, COOH group or a free or functionally modified CHO group or a CH$_2$OCH$_2$C$_6$H$_5$ group, can be treated with a reducing agent, or a compound of Formula IV, wherein Y is a CH$_2$Hal group or an esterified or etherified CH$_2$OH group can be treated with a solvolysing, in particular a hydrolysing agent, or a compound of Formula IV, wherein Y is an aminomethyl group, can first be converted, using nitrous acid or a derivative thereof, into the corresponding diazonium compound, which can be converted in the presence of R$^4$—OH into the desired compound of Formula I.

Some of the starting compounds of Formula IV are known. They can be prepared by methods which are in themselves known, for example, by reacting the phenols II with compounds of the formula X—CR$^1$R$^2$—Y under the conditions described above for the reaction of the phenols II with the compounds of Formula III.

Catalytic hydrogenation or complex metal hydrides are preferably used for the reduction. It is also possible to use other conventional reducing agents, for example, metals together with acids or bases.

Noble metal, nickel or cobalt catalysts, for example, are suitable for catalytic hydrogenations and, in addition, mixed catalysts, such as copper-chromium oxide, are also suitable for the reduction of carboxylic acid derivatives. Noble metals which can be used are, primarily, platinum and palladium, which can be present on supports (for example, charcoal, calcium carbonate or strontium carbonate), as oxides or in the finely divided form. Nickel and cobalt catalysts are preferably employed as Raney metals. The hydrogenation can be carried out at pressures between about 1 and 100 atmospheres and at temperatures between about −80° and +150° C., preferably between 20° and 100° C. The reaction can be carried out in the acid, neutral or basic range, preferably in the presence of a solvent. Suitable solvents are those mentioned above and also, for example, esters such as ethyl acetate and carboxylic acids such as acetic acid or propionic acid.

Complex metal hydrides, such as $LiAlH_4$, can also be employed as reducing agents. In this case, catalysts such as $BF_3$, $AlCl_3$ or LiBr can be added. In particular, the carboxylic acids and their esters are advantageously reduced by means of $LiAlH_4$. Suitable solvents for this purpose are, in particular, ethers such as diethyl ether, THF, di-n-butyl ether or ethylene glycol dimethyl ether and suitable solvents for the reduction with $NaBH_4$, on the other hand, are alcohols such as methanol or ethanol. The reduction is preferably carried out at temperatures between $-80°$ and $+100°$ C. The metal complexes formed are decomposed in the customary manner, for example by means of moist ether, ethyl acetate or an aqueous ammonium chloride solution. Other hydrides which are suitable for the reduction and which are essentially employed under the same conditions are, for example, calcium borohydride, magnesium borohydride, sodium aluminum hydride, lithium alkoxy-aluminum hydrides and sodium alkoxyaluminum hydrides and sodium trialkoxy-borohydrides, for example, sodium trimethoxy-borohydride. Dialkyl-aluminum hydrides, for example, diisobutyl-aluminum hydride, are also suitable as reducing agents.

A further method of reduction which can be used is the reaction with nascent hydrogen. This can be generated, for example, by treating metals with acids or bases. Thus, for example, systems such as zinc/acid, zinc/alkali metal hydroxide solution, iron/acid and tin/acid can be used. Suitable acids are, for example, hydrochloric acid and acetic acid. Sodium or another alkali metal in a lower alkanol, such as ethanol, isopropanol, n-butanol, amyl alcohol, or isoamyl alcohol, or in phenol, and also an aluminum-nickel alloy in an alkaline aqueous solution, optionally with the addition of methanol, and sodium amalgam or aluminum amalgam in an aqueous-alcoholic or aqueous solution are also suitable for generating nascent hydrogen. With this method of reduction the reaction is carried out at temperatures between about 0° and about 150° C., preferably between 20° and 120° C.

Alcohols of Formula I ($R^4 = H$) are also obtained by saponifying halogen compounds or esters of the Formula IV ($Y = CH_2Hal$ or an esterified $CH_2OH$ group) in an aqueous or aqueous-alcoholic solution or suspension, if necessary with the addition of a solubilizing agent. Examples of suitable solubilizing agents are lower alcohols, glycols and polyglycol ethers. The saponifying agents used are preferably alkalis such as NaOH or KOH, as well as suspensions of $Ca(OH)_2$. It is also possible to convert compounds of Formula IV ($Y = CH_2Hal$) by solvolysis into esters of Formula I ($R^4 = Ac$), by reacting them in aqueous, aqueous-alcoholic or alcoholic solution with alkali metal salts of fatty acids of the formula AcOH. The solvolysis or hydrolysis is preferably carried out at temperatures between about 0° and 150° C., preferentially between 60° and 120° C.

When amines of Formula IV ($Y = CH_2NH_2$) are treated with nitrous acid or a derivative thereof, for example, an alkyl nitrite or NOCl, the corresponding diazonium compounds are formed. These can be split in the presence of water by known methods, to give alcohols of Formula I ($R^4 = H$). Advantageously, an aqueous solution of $NaNO_2$ is combined, at temperatures between 0° and 100° C., with a solution of the amine in a mineral acid or acetic acid and the reaction is brought to completion by heating. If the reaction is carried out in the presence of fatty acids of the formula AcOH, for example, acetic acid, the esters of Formula I ($R^4 = Ac$) are obtained as the reaction products.

In a resulting ester of Formula I ($R^4 = Ac$), the AcO group can, if desired, be saponified, preferably under similar or identical conditions to those of the solvolysis described above. Preferably the esters are treated for about 1-48 hours with potassium carbonate in methanol, ethanol or isopropanol at temperatures between about 20° and 80° C.

Conversely, in a resulting alcohol of Formula I ($R^4 = H$), the hydroxyl group can, if desired, be esterified with a fatty acid of the formula AcOH by methods described in the literature. Suitable fatty acids are acetic acid, propionic acid, butyric acid and isobutyric acid. The esterification is preferably carried out in the presence of an acid catalyst, for example, in the presence of hydrochloric acid, sulphuric acid or p-toluenesulphonic acid, and in the presence or absence of an inert solvent, such as benzene, toluene or xylene, at temperatures between about 0° and about 140° C. During the esterification, the water of reaction can be removed azeotropically or can be chemically bonded, for example, by addition of carbodiimides.

Alcohols of Formula I ($R^4 = H$) or the corresponding alcoholates, in particular the alkali metal alcoholates, can also be reacted with the halides or anhydrides of the fatty acids, mentioned, for example, acetyl chloride or acetic anhydride. In this case an acid-binding agent, for example, NaOH, KOH, $Na_2CO_3$, $K_2CO_3$ or pyridine can be added. Examples of suitable solvents are ether, THF or benzene. An excess of the halides or anhydrides or, in particular, pyridine can also be used as the solvent. This type of esterification is also carried out at temperatures between about 0° and about 140° C.

Esters of Formula I ($R^4 = Ac$) can also be obtained by reacting the corresponding alcohols with ketenes or by transesterification in accordance with methods which are in themselves known.

The basic compounds amongst compounds of Formula I can be converted, using acids, into the corresponding acid addition salts. Acids which can be used for this reaction are those which give physiologically acceptable salts. Suitable acids are thus organic or inorganic acids, for example, aliphatic, alicyclic, araliphatic, aromatic or heterocyclic monobasic or polybasic carboxylic or sulphonic acids, such as formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulphamic acid, benzoic acid, salicylic acid, 3-phenylpropionic acid, citric acid, gluconic acid, ascorbic acid, nicotinic acid, isonicotinic acid, methanesulphonic acid or ethanesulphonic acid, ethanedisulphonic acid, 2-hydroxyethanesulphonic acid, benzenesulphonic acid, p-toluenesulfonic acid, naphthalenemonosulphonic acids and naphthalene-disulphonic acids, sulphuric acid, nitric acid, hydrogen halide acids, such as hydrochloric acid or hydrobromic acid, or phosphoric acids such as orthophosphoric acid. The free base of Formula I can, if desired, be liberated from their salts by treatment with strong bases, such as sodium hydroxide or potassium hydroxide, sodium carbonate and potassium carbonate.

If the compounds of Formula I possess a center of asymmetry, they are generally obtained in their racemic form. If the compounds have two or more centers of asymmetry, they are then generally obtained from the synthesis as mixtures of racemates, from which the individual racemates can be isolated, for example, by repeated recrystallization from suitable solvents.

Resulting racemates can be split mechanically or chemically into their optical antipodes. Preferably diastereomers are formed from the racemic mixture by reaction with an optically active resolving agent. For example, salt diastereomers of the bases of Formula I can be formed using optically active acids, such as tartaric acid, dibenzoyltartaric acid, diacetyltartaric acid, camphorsulphonic acids, mandelic acid, malic acid or lactic acid. Due to their different solubilities, the diastereomers can be resolved and converted into the desired optically active bases. It is, of course, also possible to obtain optically active compounds by the methods described above by using starting substances which are already optically active.

The novel compounds of this invention possess valuable pharmacological properties and are well tolerated. Thus, for example, they lower one or more of abnormally high cholesterol, triglycerides and uric acid blood levels, as well as inducing liver enzymes activity, i.e., increasing the activity of enzymes in the liver.

The pharmacological activity can be demonstrated by conventional methods, the lowering of the cholesterol level being demonstrated, for example, by the method of Levine et al. (Automation in Analytical Chemistry, Technicon Symposium, 1967, Mediad, New York, pages 25–28) and the lowering of the triglyceride level being demonstrated by the method of Noble and Campbell (Clin. Chem., Vol. 16, 1970, pages 166–170), in each case in the serum of rats. Other test animals which are suitable for these pharmacological tests are, for example, mice, guinea-pigs, rabbits, dogs, pigs and apes.

The compounds of Formula I and their physiologically acceptable salts are useful as medicaments and also as intermediate products for the preparation of other medicaments. For example, oxidation of the alkanol group leads to the corresponding carboxylic acids which also have valuable cholesterol and triglyceride blood level lowering activities.

The compounds of Formula I and/or their physiologically acceptable acid addition salts can be processed, in admixture with solid, semi-liquid or liquid pharmaceutically acceptable excipients or additives and, if desired, in a mixture with further active compounds, to provide pharmaceutical preparations which can be used in human medicine or in veterinary medicine. Excipients which can be used are organic or inorganic substances which are suitable for enteral or parenteral administration or topical application and which do not react with the active compounds, for example, water, vegetable oils, benzyl alcohols, polyethylene glycols, gelatine, sugar, such as lactose, starch, magnesium stearate or calcium stearate, talc, silicic acid, cellulose, petroleum jelly and cholesterol. For example, tablets, dragees, capsules, syrups, elixirs or suppositories are suitable for enteral administration; solutions, preferably oily or aqueous solutions, and suspensions, emulsions or implants can be used for parenteral administration; and ointments, creams and powders can be used for topical application. All forms of preparations can, if desired, be sterilized or contain auxiliary agents, for example, preservatives, stabilizers or wetting agents, salts for regulating osmotic pressure, buffer substances, colorants, flavorings and/or aromic substances.

The compounds of this invention are usually administered in analogy to the known compound clofibrate (ethyl 2-p-chlorophenoxy-2-methylpropionate), preferably in a dosage between 10 and 1,000, particularly between 30 and 300 mg. per dosage unit. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1 a. 2.3 g. of sodium are dissolved in 100 ml. of absolute ethanol, 22.05 g. of 4-(4-chlorophenoxy)-phenol are introduced and 9.45 g. of 2-chloro-propanol are added dropwise and the mixture is boiled for 12 hours. It is then evaporated, water is added to the residue and the aqueous solution is extracted with ether. The ether solution is washed, dried and evaporated. This gives 2-[4-(4-chlorophenoxy)-phenoxy]-propanol as a colorless oil; $n_D^{20}$ 1.5638.

Similarly,
2-[4-(4-fluorophenoxymethyl)-phenoxy]-propanol,
2-[4-(4-fluorophenoxymethyl)-phenoxy]-2-methyl-propanol, m.p. 108°–109°;
2-[4-(4-fluorophenoxymethyl)-phenoxy]-2-phenyl-ethanol,
2-[4-(4-fluorophenoxymethyl)-phenoxy]-2-phenyl-propanol,
2-[4-(4-chlorophenoxymethyl)-phenoxy]-propanol, m.p. 77°–78°,
2-[4-(4-chlorophenoxymethyl)-phenoxy]-2-methyl-propanol, m.p. 67°–70°;
2-[4-(4-chlorophenoxymethyl)-phenoxy]-2-phenyl-ethanol,
2-[4-(4-chlorophenoxymethyl)-phenoxy]-2-phenyl-propanol,
2-[4-(4-bromophenoxymethyl)-phenoxy]-propanol,
2-[4-(4-bromophenoxymethyl)-phenoxy]-2-methyl-propanol,
2-[4-(4-bromophenoxymethyl)-phenoxy]-2-phenyl-ethanol,
2-[4-(4-bromophenoxymethyl)-phenoxy]-2-phenyl-propanol,
2-[4-(1,2,3,4-tetrahydro-1-naphthyl)-phenoxy]-propanol,
2-[4-(1,2,3,4-tetrahydro-1-naphthyl)-phenoxy]-2-methyl-propanol,
2-[4-(1,2,3,4-tetrahydro-1-naphthyl)-phenoxy]-2-phenyl-ethanol,
2-[4-(1,2,3,4-tetrahydro-1-naphthyl)-phenoxy]-2-phenyl-propanol,
2-[4-(1-pyrryl)-phenoxy]-propanol,
2-[4-(1-pyrryl)-phenoxy]-2-methyl-propanol,
2-[4-(1-pyrryl)-phenoxy]-2-phenyl-ethanol,
2-[4-(1-pyrryl)-phenoxy]-2-phenyl-propanol,
2-(4-piperidino-phenoxy)-propanol,
2-(4-piperidino-phenoxy)-2-methyl-propanol,
2-(4-piperidino-phenoxy)-2-phenyl-ethanol,
2-(4-piperidino-phenoxy)-2-phenyl-propanol,
2-(4-isoindolino-phenoxy)-propanol,
2-(4-isoindolino-phenoxy)2-methyl-propanol, m.p. 175°–177°;
2-(4-isoindolino-phenoxy)-2-phenyl-ethanol and 2-(4-isoindolino-phenoxy)-2-phenyl-propanol, are obtained analogously from the corresponding phenols of Formula II using 2-chloropropanol, 2-chloro-2-methyl-propanol, 2-chloro-2-phenylethanol, 2-chloro-2-phenylpropanol or the corresponding bromo-alcohols.

b. A solution of 1 g. of 2-[4-(4-chlorophenoxy)-phenoxy]-propanol, 5 ml. of pyridine and 5 ml. of acetic anhydride is left to stand for 24 hours. The solution is evaporated and worked up in the customary manner to give 2-[4-(4-chlorophenoxy)-phenoxy]-propyl acetate; $n_D^{20}$ 1.5550.

2-[4-(4-fluorophenoxymethyl)-phenoxy]-propyl acetate,

2-[4-(4-fluorophenoxymethyl)-phenoxy]-2-methyl-propyl acetate,

2-[4-(4-fluorophenoxymethyl)-phenoxy]-2-phenyl-ethyl acetate,

2-[4-(4-fluorophenoxymethyl)-phenoxy]-2-phenyl-propyl acetate,

2-[4-(4-chlorophenoxymethyl)-phenoxy]-propyl acetate,

2-[4-(4-chlorophenoxymethyl)-phenoxy]-2-methyl-propyl acetate,

2-[4-(4-chlorophenoxymethyl)-phenoxy]-2-phenyl-ethyl acetate,

2-[4-(4-chlorophenoxymethyl)-phenoxy]-2-phenyl-propyl acetate,

2-[4-(4-bromophenoxymethyl)-phenoxy]-propyl acetate,

2-[4-(4-bromophenoxymethyl)-phenoxy]-2-methyl-propyl acetate,

2-[4-(4-bromophenoxymethyl)-phenoxy]-2-phenyl-ethyl acetate,

2-[4-(4-bromophenoxymethyl)-phenoxy]-2-phenyl-propyl acetate,

2-[4-(1,2,3,4-tetrahydro-1-naphthyl]-phenoxy-propyl acetate,

2-[4-(1,2,3,4-tetrahydro-1-naphthyl]-phenoxy-2-methyl-propyl acetate,

2-[4-(1,2,3,4-tetrahydro-1-naphthyl)-phenoxy]-2-phenyl-ethyl acetate,

2-[4-(1,2,3,4-tetrahydro-1-naphthyl)-phenoxy]-2-phenyl-propyl acetate,

2-[4-(1-pyrryl)-phenoxy]-propyl acetate,

2-[4-(1-pyrryl)-phenoxy]-2-methyl-propyl acetate,

2-[4-(1-pyrryl)-phenoxy]-2-phenyl-ethyl acetate,

2-[4-(1-pyrryl)-phenoxy]-2-phenyl-propyl acetate, 2-(4-piperidino-phenoxy)-propyl acetate, 2-(4-piperidino-phenoxy)-2-methyl-propyl acetate, 2-(4-piperidino-phenoxy)-2-phenyl-ethyl acetate, 2-(4-piperidino-phenoxy)-2-phenyl-propyl acetate, 2-(4-isoindolino-phenoxy)-propyl acetate, 2-(4-isoindolino-phenoxy)-2-methyl-propyl acetate, 2-(4-isoindolino-phenoxy)-2-phenyl-ethyl acetate and 2-(4-isoindolino-phenoxy)-2-phenyl-propyl acetate are obtained analogously from the corresponding alcohols.

c. 2-[4-(4-Chlorophenoxy)-phenoxy]-propyl propionate, 2-[4-(4-chlorophenoxy)-phenoxy]-propyl-butyrate and 2-[4-(4-chlorophenoxy)-phenoxy]-propyl isobutyrate are obtained analogously to (b) using propionic acid anhydride, butyric acid anhydride and isobutyric acid anhydride.

EXAMPLE 2 a. 2-[4-(Methyl-1,2,3,4-tetrahydro-4-quinolyl)-phenoxy]-2-methyl-propanol, m.p. 92°-94° C. is obtained analogously to Example 1 from 1-methyl-4-p-hydroxyphenyl-1,2,3,4-tetrahydroquinoline and 2-bromo-2-methylpropanol in absolute methanol in the presence of sodium methylate (48 hours).

Similarly,

2-[4-(1,2,3,4-Tetrahydroquinolino)-phenoxy]-propanol,

2-[4-(1,2,3,4-tetrahydroquinolino)-phenoxy]-2-methyl-propanol,

2-[4-(1,2,3,4-tetrahydroquinolino)-phenoxy]-2-ethanol,

2-[4-(1,2,3,4-tetrahydroquinolino)-phenoxy]-2-phenyl-propanol,

2-[4-(1,2,3,4-tetrahydroquinolino)-phenoxy]-propanol,

2-[4-(1,2,3,4-tetrahydroquinolino)-phenoxy]-2-methyl-propanol,

2-[4-(1,2,3,4-tetrahydro-4-quinolyl)-phenoxy]-2-phenyl-ethanol,

2-[4-(1,2,3,4-tetrahydro-4-quinolyl)-phenoxy]-2-phenyl-propanol,

2-[4-(1-methyl-1,2,3,4-tetrahydro-4-quinolyl)-phenoxy]-propanol,

2-[4-(1-methyl-1,2,3,4-tetrahydro-4-quinolyl)-phenoxy]-2-phenyl-ethanol, $n_D^{20}$ 1.6085; hydrochloride, softening from 75° C. onwards, 2-[4-(1-methyl-1,2,3,4-tetrahydro-4-quinolyl)-phenoxy]-2-phenyl-propanol, $n_D^{20}$ 1.5955; hydrochloride, decomposition at 221° C.;

2-[4-(4-chromanyl)-phenoxy]-propanol,

2-[4-(4-chromanyl)-phenoxy]-2-methyl-propanol,

2-[4-(4-chromanyl)-phenoxy]-2-phenyl-ethanol,

2-[4-(4-chromanyl)-phenoxy]-2-phenyl-propanol,

2-[4-(4-thiochromanyl)-phenoxy]-propanol,

2-[4-(4-thiochromanyl)-phenoxy]-2-methyl-propanol,

2-[4-(4-thiochromanyl)-phenoxy]-2-phenyl-ethanol, and

2-[4-(4-thiochormanyl)-phenoxy]-2-phenyl-propanol, $n_D^{20}$ 1.6172 are obtained analogously from 1-p-hydroxyphenyl-1,2,3,4-tetrahydroquinoline, 4-p-hydroxyphenyl-1,2,3,4-tetrahydroquinoline, 1-methyl-4-p-hydroxyphenyl-1,2,3,4-tetrahydroquinoline, 4-p-hydroxyphenyl-chromane and 4-p-hydroxyphenylthiochromane using 2-bromo-propanol, 2-bromo-2-methyl-propanol, 2-bromo-2-phenyl-ethanol, 2-bromo-2-phenyl-propanol and the corresponding chloro-alcohols.

b. The following acetates are obtaned analogously to Example 1b from the alcohols mentioned under (a) by reaction with acetic anhydride:

2-[4-(1,2,3,4-Tetrahydroquinolino)-phenoxy]-propyl acetate,

2-[4-(1,2,3,4-tetrahydroquinolino)-phenoxy]-2-methyl-propyl acetate,

2-[4-(1,2,3,4-tetrahydroquinolino)-phenoxy]-2-phenyl-ethyl acetate,

2-[4-(1,2,3,4-tetrahydroquinolino)-phenoxy]-2-phenyl-propyl acetate,

2-[4-(1,2,3,4-tetrahydro-4-quinolyl)-phenoxy]-propyl acetate,

2-[4-(1,2,3,4-tetrahydro-4-quinolyl)-phenoxy]-2-methyl-propyl acetate,

2-[4-(1,2,3,4-tetrahydro-4-quinolyl)-phenoxy]-2-phenyl-ethyl acetate,

2-[4-(1,2,3,4-tetrahydro-4-quinolyl)-phenoxy]-2-phenyl-propyl acetate,
2-[4-(1-methyl-1,2,3,4-tetrahydro-4-quinolyl)-phenoxy]-propyl acetate,
2-[4-(1-methyl-1,2,3,4-tetrahydro-4-quinolyl)-phenoxy]-2-methylpropyl acetate, 2[4-(1-methyl-1,2,3,4-tetrahydro-4-quinolyl)-phenoxy]-2-phenyl-ethyl acetate, $n_D^{20}$ 1.5817,
2-[4-(1-methyl-1,2,3,4-tetrahydro-4-quinolyl)-phenoxy]-2-phenyl-propyl acetate, $n_D^{20}$ 1.5678,
2-[4-(4-chromanyl)-phenoxy]-propyl acetate,
2[4-(4-chromanyl)-phenoxy]-2-methyl-propyl acetate,
2-[4-(4-chromanyl)-phenoxy]-2-phenyl-ethyl acetate,
2-[4-(4-chromanyl)-phenoxy]-2-phenyl-propyl acetate,
2-[4-(4-thiochromanyl)-phenoxy]-propyl acetate,
2-[4-(4-thiochromanyl)-phenoxy]-2-methylpropyl acetate,
2-[4-(4-thiochromanyl)-phenoxy]-2-phenylethyl acetate and
2-[4-(4-thiochromanyl)-phenoxy]-2-phenyl-propyl acetate.

EXAMPLE 3 a. 2.3 g. of sodium are dissolved in 170 ml. of absolute isopropanol, 12.85 g. of p-chlorophenol are introduced, 13.9 g. of 2-bromo-propanol are added dropwise and the mixture is boiled for 20 hours. The mixture is evaporated and worked up using water and ether to give 2-(4-chlorophenoxy)-propanol.

Similarly,
2-(4-Fluorophenoxy)-propanol,
2-(4-fluorophenoxy)-2-phenyl-ethanol,
2-(4-fluorophenoxy)-2-phenyl-propanol,
2-(4-chlorophenoxy)-2-phenyl-ethanol,
2-(4-chlorophenoxy)-2-phenyl-propanol, $n_D^{20}$ 1.5689,
2-(4-bromophenoxy)-propanol,
2-(4-bromophenoxy)-2-phenyl-ethanol,
2-(4-bromophenoxy)-2-phenyl-propanol,
2-(4-biphenylyloxy)-propanol.
2-(4-biphenylyloxy)-2-phenyl-ethanol, m.p. 126°-127° C.,
2-(4-biphenylyloxy)-2-phenyl-propanol, m.p. 138°-139° C.,
2-(4'-fluoro-4-biphenylyloxy)-propanol,
2-(4'-fluoro-4-biphenylyloxy)-2-phenyl-ethanol,
2-(4'-fluoro-4-biphenylyloxy)-2-phenyl-propanol,
2-(4'-chloro-4-biphenylyloxy)-propanol,
2-(4'-chloro-4-biphenylyloxy)-2-phenyl-ethanol,
2-(4'-chloro-4-biphenylyloxy)-2-phenyl-propanol, m.p. 131°-132° C.,
2-(4'-bromo-4-biphenylyloxy)-propanol,
2-(4'-bromo-4-biphenylyloxy)-2-phenyl-ethanol,
2-(4'-bromo-4-biphenylyloxy)-2-phenyl-propanol,
2-[4-(4-fluorophenoxy)-phenoxy]-propanol,
2-[4-(4-fluorophenoxy)-phenoxy]-2-phenyl-ethanol,
2-[4-(4-flurophenoxy)-phenoxy]-2-phenyl-propanol,
2-[4-(4-chlorophenoxy)-phenoxy]-propanol, $n_D^{20}$ 1.5638,
2-[4-(4-chlorophenoxy)-phenoxy]-2-phenyl-ethanol,
2-[4-(4-chlorophenoxy)-phenoxy]-2-phenyl-propanol,
2-[4-(4-bromophenoxy)-phenoxy]-propanol,
2-[4-(4-bromophenoxy)-phenoxy]-2-phenyl-ethanol and
2-[4-(4-bromophenoxy)-phenoxy]-2-phenyl-propanol are obtained analogously from p-fluorophenol, p-chlorophenol, p-bromophenol, 4-hydroxydiphenyl, 4'-fluoro-4-hydroxydiphenyl, 4'-chloro-4-hydroxydiphenyl or 4'-bromo-4-hydroxydiphenyl, 4'-fluoro-4-hydroxydiphenyl ether, 4'-chloro-4-hydroxydiphenyl ether or 4'-bromo-4-hydroxydiphenyl ether using the corresponding chloro alcohols, bromo-alcohols or idodo-alcohols.

b. The following acetates are obtained analogously to Example 1b by reacting the alcohols described under (a) with acetic anhydride:
2(4-Fluorophenoxy)-propyl acetate,
2-(4-fluorophenoxy)-2-phenyl-ethyl acetate,
2-(4-fluorophenoxy)-2-phenylpropyl acetate,
2-(4-chlorophenoxy)-propyl acetate,
2-(4-chlorophenoxy)-2-phenyl-ethyl acetate,
2-(4-chlorophenoxy)-2-phenyl-propyl acetate.
2-(4-bromophenoxy)-propyl acetate,
2-(4-bromophenoxy)-2-phenyl-ethyl acetate,
2-(4-bromophenoxy)-2-phenyl-propyl acetate,
2-(4-biphenyloxy)-propyl acetate,
2-(4-biphenylyloxy)-2-phenyl-ethyl acetate, m.p. 94°-96° C.,
2-(4-biphenylyloxy)-2-phenyl-propyl acetate,
2-(4'-fluoro-4-biphenyloxy)-propyl acetate,
2-(4'-fluoro-4-biphenyloxy)-2-phenyl-ethyl acetate,
2-(4'-fluoro-4-biphenylyloxy)-2-phenyl-propyl acetate,
2-(4'-chloro-4-biphenylyloxy)-propyl acetate,
2-(4'-chloro-4-biphenylyloxy)-2-phenyl-ethyl acetate,
2-(4'-chloro-4-biphenylyloxy)-2-phenyl-propyl acetate,
2-(4'-bromo-4-biphenylyloxy)-propyl acetate,
2-(4'-bromo-4-biphenylyloxy)-2-phenyl-ethyl acetate,
2-(4'-bromo-4-biphenylyloxy)-2-phenyl-propyl acetate,
2-[4-(4-fluorophenoxy)-phenoxy]-propyl acetate,
2-[4-(4-fluorophenoxy)-phenoxy]-2-phenyl-ethyl acetate,
2-[4-(4-fluorophenoxy)-phenoxy]-2-phenyl-propyl acetate,
2-[4-(4-chlorophenoxy)-phenoxy]-propyl acetate $n_D^{20}$ = 1.5550,
2-[4-(4-chlorophenoxy)-phenoxy]-2-phenyl-ethyl acetate,
2-[4-(4-chlorophenoxy)-phenoxy]-2-phenyl-propyl acetate,
2-[4-(4bromophenoxy)-phenoxy]-propyl acetate,
2-[4-(4-bromophenoxy)-phenoxy]-2-phenyl-ethyl acetate and
2-[4-(4-bromophenoxy)-phenoxy]-2-phenyl-propyl acetate.

EXAMPLE 4

21.1 g of 4-isoindolino-phenol are added to a suspension of 2.4 g of NaH in 200 ml. of dimethylacetamide. The mixture is stirred for one hour at 20° C., 15.3 g. of 2-bromo-2-methylpropanol are added and the mixture is heated to 90° C. for 20 hours. After cooling, the mixture is worked up using water and ether and gives 2-(4-isoindolino-phenoxy)-2-methylpropanol, m.p. 175°-177° C.

EXAMPLE 5

A mixture of 2.42 g. of 4p-hydroxyphenyl-thiochromane and 0.23 g. of sodium in 50 ml. of xylene is boiled for 3 hours. The mixture is allowed to cool to 20° C., 2.15 g. of 2-bromo-2-phenylpropanol in 10 ml. of xylene are added and the suspension is stirred for 6 hours at the boil, cooled and treated with 2 ml. of ethanol. The inorganic precipitate is filtered off, the filtrate is evaporated, the residue is taken up in ether and the solution is washed with NaHCO₃ solution and saturated NaCl solution, dried over MgSO₄ and evaporated, to give 2-[4-(4-thiochromanyl)-phenoxy]-2-phenylpropanol, $n_D^{20}$ 1.6172.

EXAMPLE 6

A solution of 15.3 g. of 2-bromo-2-methylpropanol in 50 ml. of acetone is added slowly to a stirred mixture consisting of 23.45 g. of 4-p-chlorophenoxymethyl-phenol, 13.8 g. of K₂CO₃ an 80 ml. of acetone. The mixture is boiled for 12 hours while stirring and then filtered and evaporated to give 2-[4-(4-chlorophenoxymethyl)-phenoxy]-2-methyl-propanol, m.p. 67°-70° C.

EXAMPLE 7

A solution of 10 g. of 2-[4-(1-methyl-1,2,3,4-tetrahydro-4-quinolyl)-phenoxy]-phenylacetic acid ethyl ester in 25 ml. of the THF is added dropwise, over the course of 30 minutes, to a solution of 1.1 g. of LiAlH₄ in 25 ml. of THF. The mixture is boiled for 3 hours, cooled, a mixture of 10 ml. of water and 40 ml. of THF and then 10 ml. of concentrated sodium hydroxide solution are added dropwise, the phases are separated and the organic phase is evaporated to give 2-phenyl-2-[4-(1-methyl-1,2,3,4-tetrahydro-4-quinolyl)phenoxy)-ethanol; $n_D^{20}$ 1.6085. Hydrochloride, softens above 75° C.

EXAMPLE 8

13.8 ml. of triethylamine are added, at 10° C., to a solution of 29.25 g. of 2-[4-(4-chlorophenoxy)-phenoxy]-propionic acid in 200 ml. of THF. The mixture is cooled to −10° C., a solution of 9.8 ml. of chloroformic acid ethyl ester in 60 ml, of THF is added dropwise and the mixture is stirred for 1 hour at −10° C. The solution contains 1-[4-(4-chlorophenoxy)-phenoxy]-4,6-dioxaoctane-3,5-dione, which is not isolated. 7.4 g. of NaBH₄ are then introduced in portions. The mixture is stirred for 30 minutes at −10° C. and for 30 minutes at 0° C., poured into water and extracted with chloroform. After evaporation of the extract, the residue is boiled for 1 hour with 200 ml. of 6% ethanolic potassium hydroxide solution, the mixture is evaporated and worked up with water and ether to give 2-[4-(4-chlorophenoxy)-phenoxy]-propanol.

EXAMPLE 9

A solution of 3.2 g. of 2-[4-(4-chlorophenoxymethyl)-phenoxy]-2-methylpropionic acid in 20 ml. of absolute THF is added dropwise to a mixture of 0.57 g. of LiAlH₄ in 20 ml. of absolute THF. The mixture is boiled for 8 hours, 2 ml. of water in 3 ml. of THF and 4 ml. of 25% sodium hydroxide solution are added, the liquid is decanted off and the residue is washed with ether. Drying, filtering and evaporating the combined organic phases gives 2-[4-(4-chlorophenoxymethyl)-phenoxy]-2-methyl-propanol, m.p. 67°-70° C.

EXAMPLE 10

A solution of 3.04 g. of 2-[4-(4-chlorophenoxymethyl)phenoxy]-2-methyl-propanol (obtainable by Rosenmund reduction of the corresponding acid chloride) in 15 ml. of ethanol is added dropwise to a solution of 0.6 g. of NaOH₄ in 15 ml. of ethanol. The mixture is stirred for 2 hours at 20° C. and worked up in the usual manner to give 2-[4-(4-chlorophenoxymethyl)-phenoxy]-2-methyl-propanol, m.p. 67°-70° C.

EXAMPLE 11

A solution of 3.53 g. of 2-methyl-2-(4-]1-methyl-1,2,3,4-tetrahydro-4-quinolyl)-phenoxyl]-propionic acid ethyl ester in 20 ml. of hexane is added dropwise to a solution of 0.73 g. of diisobutyl-aluminum hydride in 15 ml. of absolute hexane. The mixture is stirred for a further hour at −70° C., decomposed with aqueous ammonium chloride solution, the hexane phase is separated off and the aqueous phase is extracted with ether. The ether/hexane solution is dried and evaporated. Chromatography of the residue on silica gel using benzene/hexane (9:1) gives 2-methyl-2-[4-(1-methyl-1,2,3,4-tetrahydro-4-qinolyl)-phenoxy]-propanol, m.p. 92°-94° C.

EXAMPLE 12

2.89 g. of 2-(biphenylyl-4-oxy)-2-phenyl-ethylamine (obtainable by reacting 4-hydroxy-biphenyl with 2-bromophenylacetenitile and subsequently reducing the resulting nitrile) are dissolved in 50 ml. of 15% aqueous acetic acid and a solution of 1 g. of NaNO₂ in 5 ml. of water is added while cooling with ice. The mixture is heated at 80° C. for 1 hour, worked up in the usual manner and purified by chromatography on silica gel to give 2-(4-biphenylyloxy)-2-phenyl-ethanol, m.p. 126°-127° C.

EXAMPLE 13 a. 3 g. of 2-[4-(1-methyl-1,2,3,4-tetrahydro-4-quinolyl)-phenoxy]-2-methyl-propyl bromide are dissolved in 20 ml. of DMF, 3 g. of anhydrous potassium acetate are added and the mixture is stirred for 3 hours at 60° C. Working up in the usual manner gives 2-[4-(1-methyl-1,2,3,4-tetrahydro-4-quinolyl)-phenoxy]-2-methyl-propyl acetate.

b. 1 g. of the acetate obtained according to (a) is boiled for 8 hours with 0.5 g. of K₂CO₃ in 20 ml. of methanol. Working up in the usual manner gives 2-[4-(1-methyl-1,2,3,4-tetrahydro-4-quinolyl)-phenoxy]-2-methyl-propanol, m.p. 92°-94° C.

EXAMPLE 14

2 g. of 2-[4-(1-methyl-1,2,3,4-tetrahydro-4-quinolyl)-phenoxy]-2-methyl-propyl benzyl ether (obtainable from the corresponding bromine compound and sodium benzylate) are dissolved in 25 ml. of methanol and hydrogenated on 0.2 g. of 5% Pd-C-catalyst at 20° C. until the absorption of hydrogen ceases. The solution is filtered off and evaporated to give 2-[4-(1-methyl-1,2,3,4-tetrahydro-4-quinolyl)-phenoxy-2-methyl-propanol, m.p. 92°-94° C.

The examples which follow relate to pharmaceutical preparations which contain compounds of Formula I.

EXAMPLE A - Tablets

A mixture consisting of 300 kg of 2-[4-chlorophenoxy-methyl)-phenoxy]-2-methyl-propanol, 500 kg. of lactose, 160 kg. of corn starch, 20 kg. of cellulose powder and 20 kg. of magnesium stearate is pressed in the usual manner into tablets, each of which contains 300 mg. of the active compound.

EXAMPLE B - Drawings

Tablets are pressed analogously to Example A and are then coated in the customary manner with a coating consisting of sugar, corn starch, talc and tragacanth.

Tablets and dragees which contain one or more of the other active compounds of Formula I or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound selected from the group consisting of 2-[4-(4-chloro-phenoxy)-phenoxy]-propanol, 2-[4-(4-chlorophenoxymethyl)-phenoxy]-2-methyl-propanol, 2-[4-(4-chlorophenoxy)-phenoxy]-2-phenyl-propanol, 2-(4-biphenylyloxy)-2-phenyl-ethanol, 2-(4-biphenylyloxy)-2-phenyl-propanol, 2-(4'-chloro-4-biphenylyloxy)-2-phenyl-propanol, 2-(4-biphenylyloxy)-2-phenyl-ethyl acetate, 2-[4-(4-chlorophenoxy)-phenoxy]-propyl acetate, 2-[4-(4-fluorophenoxymethyl)-phenoxy]-2-methyl-propanol, and 2-[4-(4-chlorophenoxymethyl)-phenoxy]-propanol.

2. A compound of claim 1, 2-[4-(4-chlorophenoxymethyl)-phenoxy]-2-methyl-propanol.

3. A compound of claim 1, 2-[4-(4-chlorophenoxy)-phenoxy]-2-phenyl-propanol.

4. A compound of claim 1, 2-(4-biphenylyloxy)-2-phenyl-ethanol.

5. A compound of claim 1, 2-(4-biphenylyloxy)-2-phenyl-propanol.

6. A compound of claim 1, 2-(4'-chloro-4-biphenylyloxy)-2-phenyl-propanol.

7. A compound of claim 1, 2-(4-biphenylyloxy)-2-phenyl-ethyl acetate.

8. A compound of claim 1, 2-[4-(4-chlorophenoxy)-phenoxy]-propyl acetate.

9. 2-[4-(4-Fluorophenoxymethyl)-phenoxy]-2-methyl-propanol, a compound of claim 1.

10. 2-[4-(4-Chlorophenoxymethyl)-phenoxy]-propanol, a compound of claim 1.

11. 2-[4-(4-Chloro-phenoxy)-phenoxy]-propanol, a compound of claim 1.

* * * * *

UNITED STATES PATENT AND TRADEMARK OFFICE
CERTIFICATE OF CORRECTION

PATENT NO. : 4,051,173
DATED : September 27, 1977
INVENTOR(S) : ERICH SCHACHT ET AL.

It is certified that error appears in the above-identified patent and that said Letters Patent are hereby corrected as shown below:

Column 16, line 9: Change "biphenyloxy" to --biphenylyloxy--.

Column 16, line 11: Change "biphenyloxy" to --biphenylyloxy--.

Signed and Sealed this

Thirty-first Day of January 1978

[SEAL]

Attest:

RUTH C. MASON
Attesting Officer

LUTRELLE F. PARKER
Acting Commissioner of Patents and Trademarks